US012414889B2

(12) United States Patent
Grothem

(10) Patent No.: US 12,414,889 B2
(45) Date of Patent: Sep. 16, 2025

(54) PATIENT INTUBATING PARTITION SPHERE

(71) Applicant: LGI, LLC, Lakeville, MN (US)

(72) Inventor: Larissa Grothem, Lakeville, MN (US)

(73) Assignee: LGI, LLC, Lakeville, MN (US)

( * ) Notice: Subject to any disclaimer, the term of this patent is extended or adjusted under 35 U.S.C. 154(b) by 1006 days.

(21) Appl. No.: 17/366,833

(22) Filed: Jul. 2, 2021

(65) Prior Publication Data

US 2022/0000694 A1 Jan. 6, 2022

Related U.S. Application Data

(60) Provisional application No. 63/048,403, filed on Jul. 6, 2020.

(51) Int. Cl.
*A61G 10/00* (2006.01)
*A61G 10/02* (2006.01)
*A61M 16/04* (2006.01)

(52) U.S. Cl.
CPC ......... *A61G 10/005* (2013.01); *A61G 10/023* (2013.01); *A61M 16/0488* (2013.01)

(58) Field of Classification Search
CPC .............. A61G 10/005; A61G 10/023; A61M 16/0488; A61M 16/0066; A61M 16/0093; A61M 16/0627; A61M 16/009; A61M 16/1055; A61M 16/1065; A61M 16/107; A61M 16/208; A61M 2202/0208; A61M 2205/8206; A61M 2209/00; A61B 90/05; B25J 21/02

USPC ....................................................... 600/20–21
See application file for complete search history.

(56) References Cited

U.S. PATENT DOCUMENTS

| | | |
|---|---|---|
| 3,265,059 A | 8/1966 | Matthews |
| 3,272,199 A | 9/1966 | Matthews |
| 3,818,896 A * | 6/1974 | Deaton ............... A61G 11/009 600/22 |
| 5,832,919 A * | 11/1998 | Kano .................. A61G 10/005 600/20 |
| 5,950,625 A * | 9/1999 | Bongiovanni ......... A61B 90/40 128/845 |
| 6,217,507 B1 * | 4/2001 | Bonvik ............... A61G 10/005 600/21 |
| 6,461,290 B1 | 10/2002 | Reichman et al. |
| 10,905,839 B1 * | 2/2021 | Bui .................... A61M 16/0672 |
| 2004/0158121 A1 * | 8/2004 | Ford .................... B08B 15/026 600/21 |
| 2004/0255937 A1 | 12/2004 | Sun |
| 2005/0085686 A1 | 4/2005 | Yuen |
| 2008/0020695 A1 * | 1/2008 | Chang .................. B08B 15/026 55/385.2 |
| 2008/0319249 A1 * | 12/2008 | Kuo ..................... A61F 7/0053 600/22 |

(Continued)

*Primary Examiner* — Sunita Reddy
(74) *Attorney, Agent, or Firm* — Christopher J. Knors; Moore & Van Allen PLLC

(57) ABSTRACT

A disposable, isolating intubation device is described, the device comprising a flexible, spherical compartment inflatable from a collapsible state, the flexible, spherical compartment being substantially transparent and having a closed end and an open end distal from the closed end defining an inside volume for receiving a head, shoulders and a portion of a torso of a patient and methods of using.

17 Claims, 9 Drawing Sheets

(56) References Cited

U.S. PATENT DOCUMENTS

| | | | |
|---|---|---|---|
| 2016/0074268 A1* | 3/2016 | Breegi | A61G 11/009 600/21 |
| 2016/0107006 A1* | 4/2016 | Giulianotti | A61M 16/0627 128/201.28 |
| 2021/0298979 A1* | 9/2021 | Klein | A61G 10/023 |
| 2021/0307985 A1* | 10/2021 | Staab | A61G 10/005 |
| 2021/0322243 A1* | 10/2021 | Hamilton | A61G 10/023 |
| 2021/0322244 A1* | 10/2021 | Moore | E04H 15/20 |
| 2021/0353150 A1* | 11/2021 | Wood | A61B 90/05 |
| 2021/0361375 A1* | 11/2021 | Hartman | A61B 90/05 |
| 2021/0393368 A1* | 12/2021 | Reyes | A61B 90/40 |
| 2023/0032878 A1* | 2/2023 | Kota | A61B 5/097 |
| 2023/0293260 A1* | 9/2023 | Fuzy | A61G 10/005 600/21 |

* cited by examiner

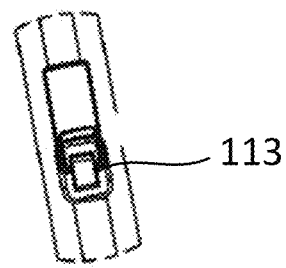
FIG. 4
FIG. 5
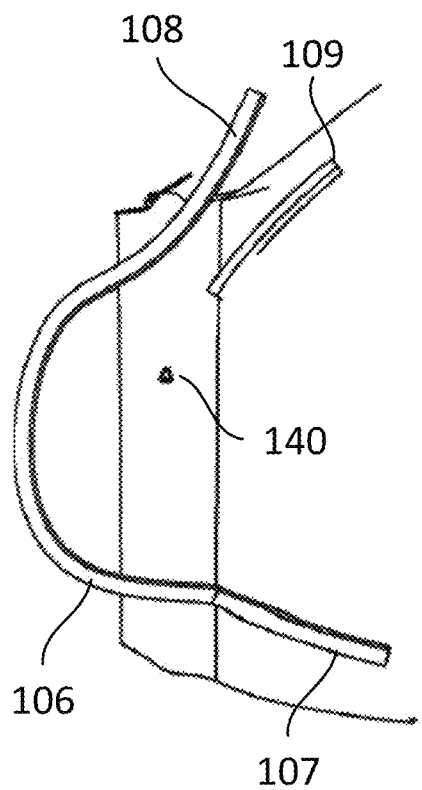
FIG. 6

PATIENT INTUBATING PARTITION SPHERE

CROSS-REFERENCE TO RELATED APPLICATIONS

This application claims the benefit of U.S. Provisional Application No. 63/048,403 filed on Jul. 6, 2020, the entirety of which is incorporated herein by reference.

TECHNICAL FIELD

This disclosure relates to Patient Intubating Partition Spheres (PIPS), e.g., protective intubation devices used to isolate contagious patients from health care professionals, and particularly, airway management personnel. This intubation device provides a barrier against air-borne chemical and biological agents by isolating the person within a plastic environment.

BACKGROUND

The use of flexible plastic, such as PVC for forming an isolation cylindrical plastic tube about a patient and for purifying the air being admitted into the enclosed volume is disclosed in U.S. Pat. Nos. 3,265,059, 3,272,199 and 6,461,290. The devices proposed in these patents are bulky or designed for transport and/or are simply not compact for storage in large numbers to be ready for use in case of a biological emergency, nor are these devices adapted to be used with a litter for transport to or for use within evacuation vehicles, either of the military type or of a fire department type.

SUMMARY

In one example a disposable, isolating intubation device is provided, the device comprising: a flexible, spherical compartment inflatable from a collapsible, folded state, the flexible, spherical compartment being substantially transparent and having a closed end and an open end distal from the closed end defining an inside volume for receiving a head, shoulders and a portion of a torso of a patient. The intubation device comprises a cuff proximal to the open end; the cuff providing for closing of the flexible, spherical compartment about the torso to provide a barrier about the patient therein; at least one inlet port on the spherical compartment configured for receiving powered air; at least one exit port on the spherical compartment configured for releasing air; at least one access port on the spherical compartment configured for coupling with medical devices; and at least one pair of gloves coupled with the spherical compartment and projecting into the inside volume.

In one aspect, the intubation device further comprises a substantially airtight zipper extending lengthwise from the cuff to at least partially between the open end and the closed end. In another aspect, alone or in combination with any of the previous aspects, the intubation device further comprises at least one selectively openable hatch on the flexible spherical compartment for receiving and removing objects from the inside volume.

In another aspect, alone or in combination with any of the previous aspects, the spherical compartment is comprised of a transparent polymeric material.

In another aspect, alone or in combination with any of the previous aspects, the cuff comprises at least two securing straps spaced from each other, the at least two securing straps proximally coupled to the spherical compartment on a first side and distally securable to this spherical compartment on a second side.

In another aspect, alone or in combination with any of the previous aspects, the cuff comprises an adhesive or cohesive surface for adhering to the patient.

In another aspect, alone or in combination with any of the previous aspects, the cuff comprises a inflation port configured to receive air and to inflate the cuff.

In another aspect, alone or in combination with any of the previous aspects, the at least one inlet port receives air from an air blowing device at an airflow rate to inflate the flexible spherical compartment and maintains separation from at least a portion of the flexible spherical compartment and the patient's body.

In another aspect, alone or in combination with any of the previous aspects, the at least one inlet port receives air from a powered air purifying respirator (PAPR) or self-contained breathing device.

In another aspect, alone or in combination with any of the previous aspects, the at least one inlet port is a one-way airflow device to prevent a reverse flow of air from the inside volume.

In another aspect, alone or in combination with any of the previous aspects, the at least one exit port is a one-way airflow device to prevent a reverse flow of air from the ambient environment. In another aspect, alone or in combination with any of the previous aspects, the at least one exit port is coupled to a reservoir. In another aspect, alone or in combination with any of the previous aspects, the at least one exit port is coupled to an expandable reservoir.

In another aspect, alone or in combination with any of the previous aspects, the at least one inlet port and/or the at least one exit port further comprises at least one filter for filtering air being presented to the inside volume or air exiting therefrom, respectively.

In another aspect, alone or in combination with any of the previous aspects, the at least one filter is configured to reduce or eliminate introduction of an infectious disease from the ambient atmosphere or to the ambient atmosphere.

In another aspect, alone or in combination with any of the previous aspects, the at least one access port receives intubation equipment, optical equipment, an oxygen line, a suction line, or electrical leads.

In another aspect, alone or in combination with any of the previous aspects, the at least one pair of gloves is positioned in proximity to the patient's head.

In another example, a method of intubating a patient is provided, the method comprising the steps of introducing at least a portion of a patient to the inside volume of the device of any one of previous aspects; securing at least a portion of the cuff to at least a portion of the patient's torso; connecting powered air to the at least one inlet port; inflating the inside volume; and coupling at least one medical device to the at least one access port; wherein the patient's respiratory orifices are isolated from an ambient environment.

BRIEF DESCRIPTION OF THE DRAWINGS

FIG. 4 is an enlarged view of section 4 of FIG. 3C showing a closure member;

FIG. 5 is an enlarged view of section 5 of FIG. 3C showing an inflation valve;

FIG. 6 is an enlarged view of section 6 of FIG. 3D;

DETAILED DESCRIPTION

Figure 1A:
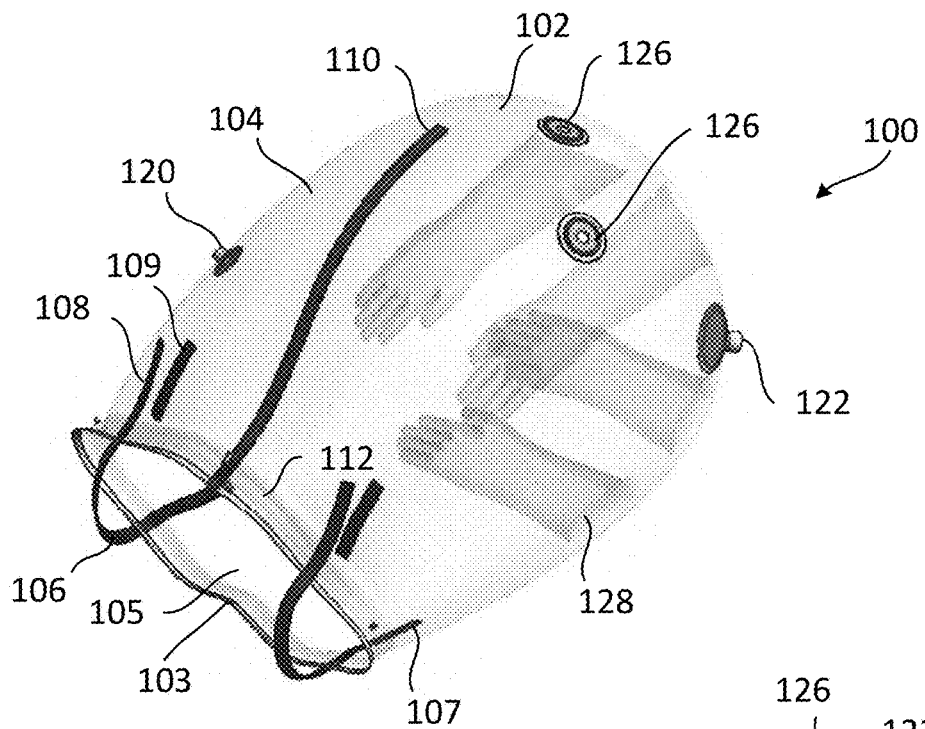
FIG. 1A is a perspective view of an exemplary Patient Intubating Partition Sphere (PIPS) apparatus in accordance with the present disclosure.

Recent highly contagious viral epidemics and pandemics such as COVID-19, SARS, MERS, EBOLA, hemorrhagic fevers have highlighted a necessity that has never adequately been addressed—how to protect airway operatives and other healthcare professionals when caring for asymptomatic or symptomatic patients in need of external airway management. Other communicable diseases for example, tuberculosis (TB) also presents an existential threat to airway management personnel that can be minimized or eliminated using the apparatus of the present disclosure.

During epidemics and/or pandemics the presently disclosed PIPS apparatus is configured to be rapidly deployed to protect healthcare professionals. The presently disclosed apparatus and system is configured to mitigate dispersal of aerosolized droplets, fomites, blood and/or other bodily fluids during (intensive) airway salvage. The presently disclosed apparatus and system is also configured for addressing additional specific situations, for example, off-gassing of industrial toxins such as hydrogen sulfide nitriles, organophosphates, or other biological toxins and/or nerve agents (sarin etc.) that may be present on the patient or be expressed by the patient by respiration. Thus, the presently disclosed apparatus and system is configured for mitigating dangers to airway managers & operating room staff by its containment of dispersed aerosolized matter or volatile gases.

In one example, the PIPS device comprises access ports for the healthcare professional or airway management personnel to interact with the patient within the device. In one example, the access ports comprise sleeves having an open proximal end for receiving a human hand and arm and a closed distal end configured to receive fingers of the human hand so as to allow access to the interior portion of the PIPS device and/or to manipulate medical devices for the care and/or treatment of the patient.

In one example, all or part of the sleeves are the same material as the material of the PIPS device. In another example, the all or part of the prefabricated sleeves are of different material than the material of the PIPS device.

In one example, all or part of the sleeves are the same thickness as the thickness of the PIPS device. In another example, the all or part of the sleeves are of a thickness that is less than the thickness of the PIPS device, for example, the fingers of the sleeve and/or wrist area can be thinner so as to provide digit/hand flexibility. In one example, the sleeves are integral with the PIPS device. In another example, the sleeves are configured for exchange or replacement.

In one example, the PIPS device provides access to its internal compartment via an access port. In one example, the access port is a tangential flap with zippers and or hook and loop (e.g., Velcro) attachment.

In one example, the PIPS device provides for attachment to the patient's torso so as to provide a seal such that an interior positive pressure is substantially maintained during use of the device. In one example, the PIPS device provides for attachment to the patient's torso using an elastic cuff. In another example, the elastic cuff is inflatable so as to provide or to further assist in sealing the device to the patient's torso.

In one example, the presently disclosed sphere 100, 200 is configured to operate without generating a positive pressure magnitude that would otherwise induce fomite egress from the dome.

The protective barrier to primarily be made of a thin plastic material which is collapsible for compact storage and inflatable after receiving a patient so as to provide a low-cost, disposable, intubation device. Further, when the patient is inside, it is important that the patient not feel claustrophobic or experience claustrophobia and, therefore, it is desirable to provide the patient with a clear field of view, as well as to have air flowing about the patient's face.

In one example, when the ambient atmosphere about the patient is contaminated, the air being supplied into the intubation device is filtered before entering the device. Stated differently, if the surrounding ambient atmosphere is contaminated, then the patient is placed within the intubation device, and that the air being supplied to the patient is purified and filtered before it is forced into the intubation device. On the other hand, if the patient has an infectious disease that can be transported by air, then it is desired to have the air from the interior of the protective device filtered or purified before it is discharged. In one example, the air from the interior of the protective device is discharged into an expandable reservoir. In another example, the air from the interior of the protective device is filtered or purified before it is discharged into an expandable reservoir. In another example, the air from the interior of the protective device is discharged into an expandable reservoir and then filtered or purified before it is released from the reservoir.

Figure 1B:
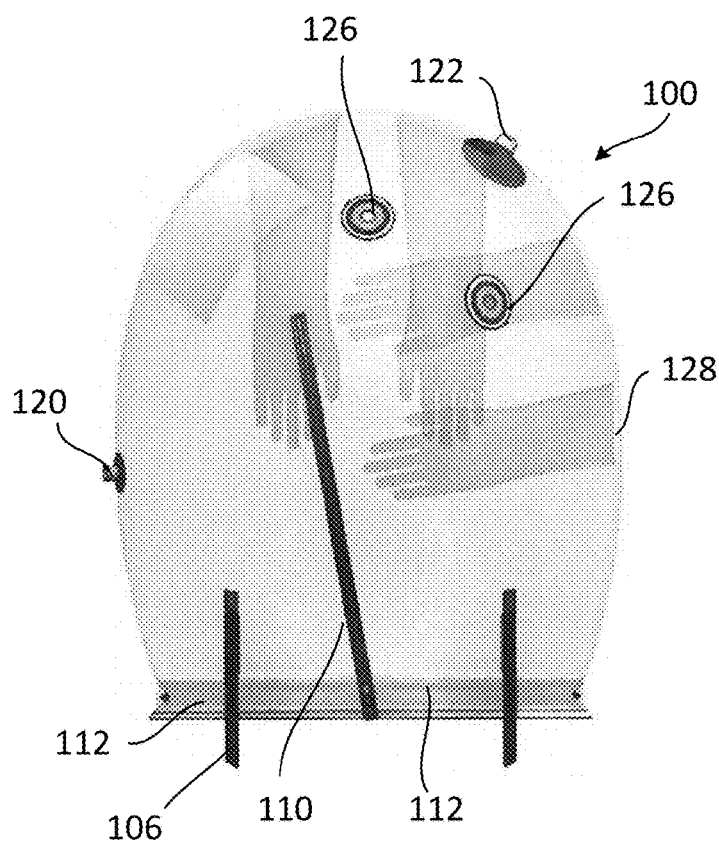
FIG. 1B is a top view of the PIPS apparatus of FIG. 1A.

Referring now to the drawings for purposes of illustration, there is illustrated in FIGS. 1A, 1B an exemplary Patient Intubating Partition Sphere (PIPS) (hereinafter also referred to as device 100 or device 200 or apparatus 100 or apparatus 200 or isolation sphere 100 or isolation sphere 200) (FIG. 3) is shown having a top surface 104 and a bottom surface 103 separated by opposing sides forming an intubation apparatus having an open end 105 for receiving at least a portion of a patient and a closed-end 102. PIPS 100 is shown with cuff 112 at open end 105. Securement members 106 are positioned adjacent open end 105. In one example, securement members 106 are securement straps as shown projecting from attachment points 107 and terminating at distal end 108. Distal end 108 of securing straps 106 is configured to secure to receiving members 109 located on an opposing side of spherical surface. PIPS 100 is shown with accessing member 110 which extends approximately from the closed-end to the open end 105 to enlarge the opening for receiving the patient. PIPS 100 is shown with a plurality of gloves 128 for attending to the patient. In one example, at least a pair of gloves 128 are present. In another example, at least two pairs of gloves are present. For the purpose of allowing the introduction of various lines into the interior of the apparatus for checking on the condition, providing fluids or medicines, and/or intubation to the patient within the PIPS 100, there is provided a plurality of small access ports discussed in more detail below. In one example, access ports in the sphere 100, 200 for intubator components and airway assistant gloves 128 are located at levels that best facilitated access to the patient, without causing dome collapse, or distortion. In one example, gloves 128 can be taped about the wrists of an operator, preventing or eliminating air leakage while maintaining patient dome inflation. In another example, gloves 128 are not taped about the wrists of an operator, thus providing rapid removal of the hand or other motion by the operator.

Figure 2A:
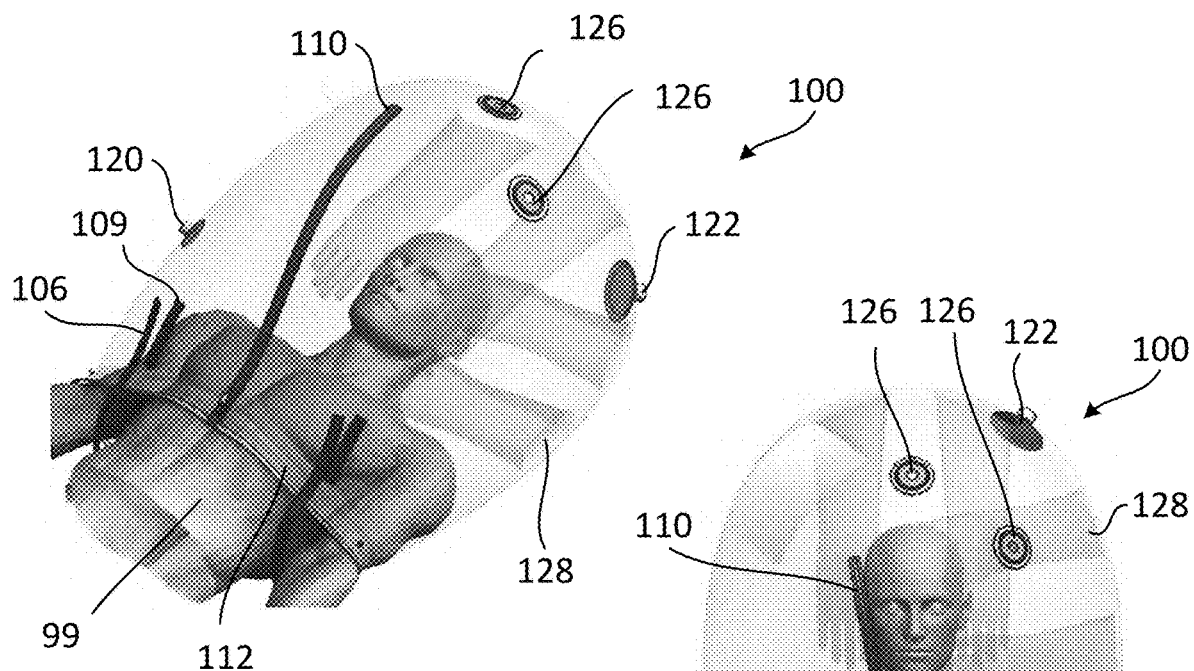
FIG. 2A is a perspective view of the PIPS apparatus in use.
Figure 2B:
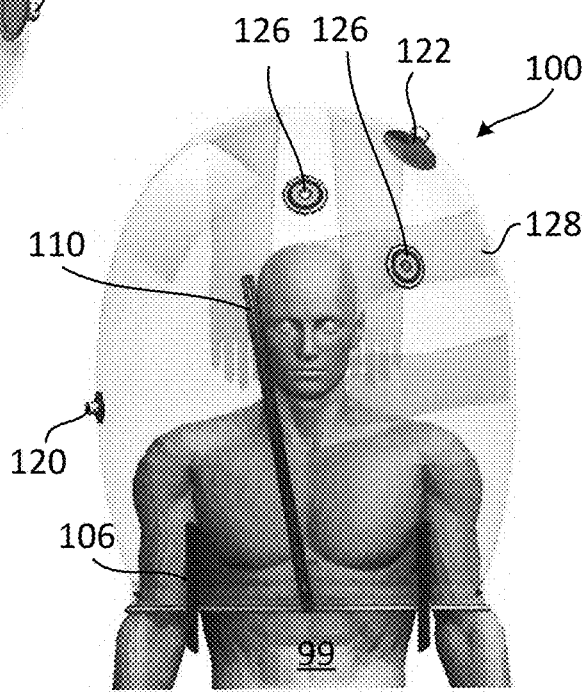
FIG. 2B is a top view of the PIPS apparatus of FIG. 2A.
Figure 2C:
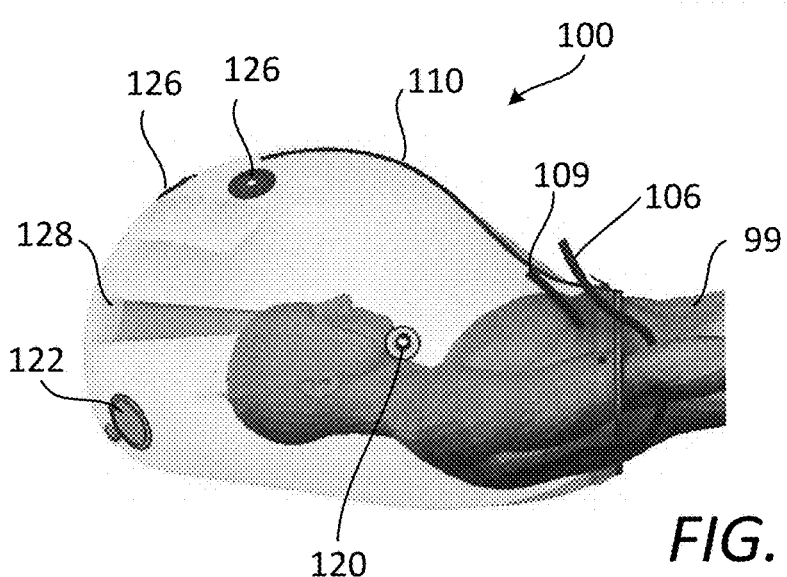
FIG. 2C is a side view of the PIPS apparatus of FIG. 2A.

FIGS. 2A, 2B, and 2C are perspective, top, and side view of the PIPS apparatus shown in operation about a patient 99. Gloves 128 are positioned about patient 99 and access ports 126 for providing treatment. Additional gloves and access ports can be used.

Figure 3A:
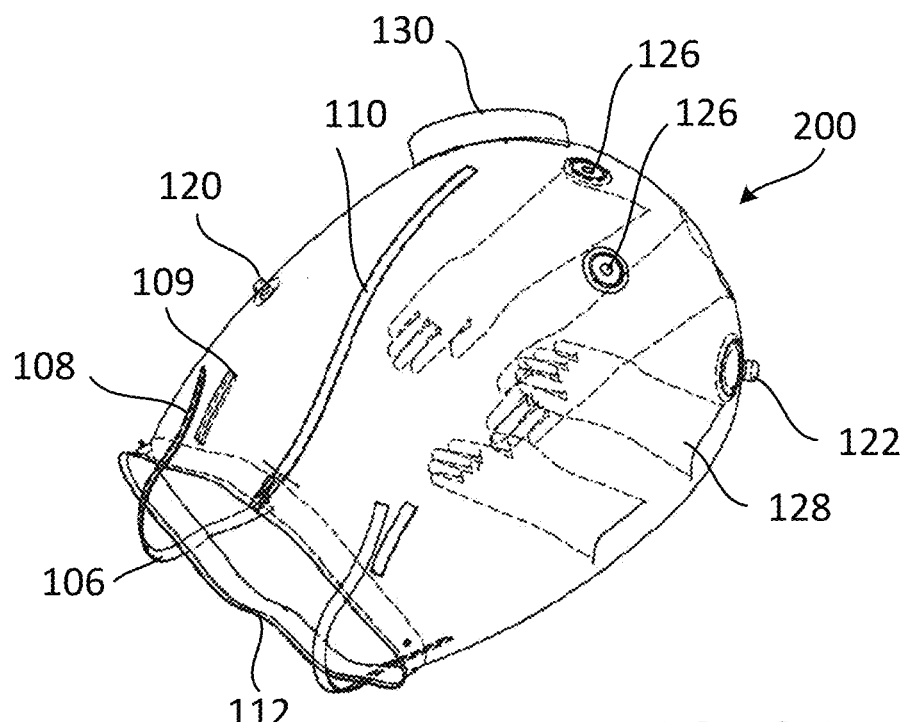
FIG. 3A is a perspective view of another exemplary Patient Intubating Partition Sphere (PIPS) apparatus in accordance with the present disclosure.
Figure 3B:
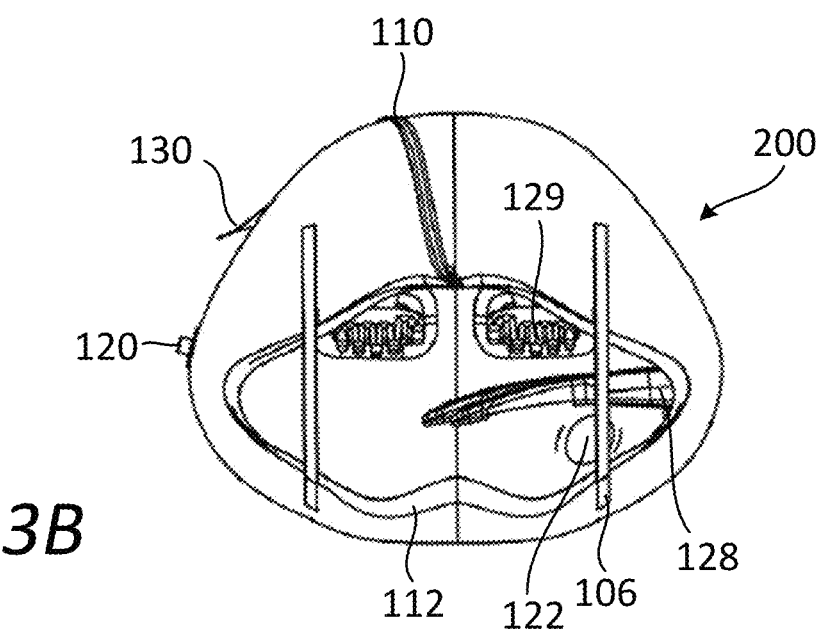
FIG. 3B is an open side view of the PIPS apparatus of FIG. 3A showing the interior of the apparatus.

FIG. 3A is a perspective view of another exemplary Patient Intubating Partition Sphere (PIPS) apparatus 200 having similar features as previously described for apparatus 100 with the addition of interior access member 130 shown in proximity to accessing member 110. Access member 130 functions as a access hatch to transport objects in and out of sphere 100,200. FIG. 3B is an open side view of the PIPS apparatus of FIG. 3A showing the interior of the apparatus, including fingers 129 of gloves 128 and inside surface of port 122.

Figure 3C:
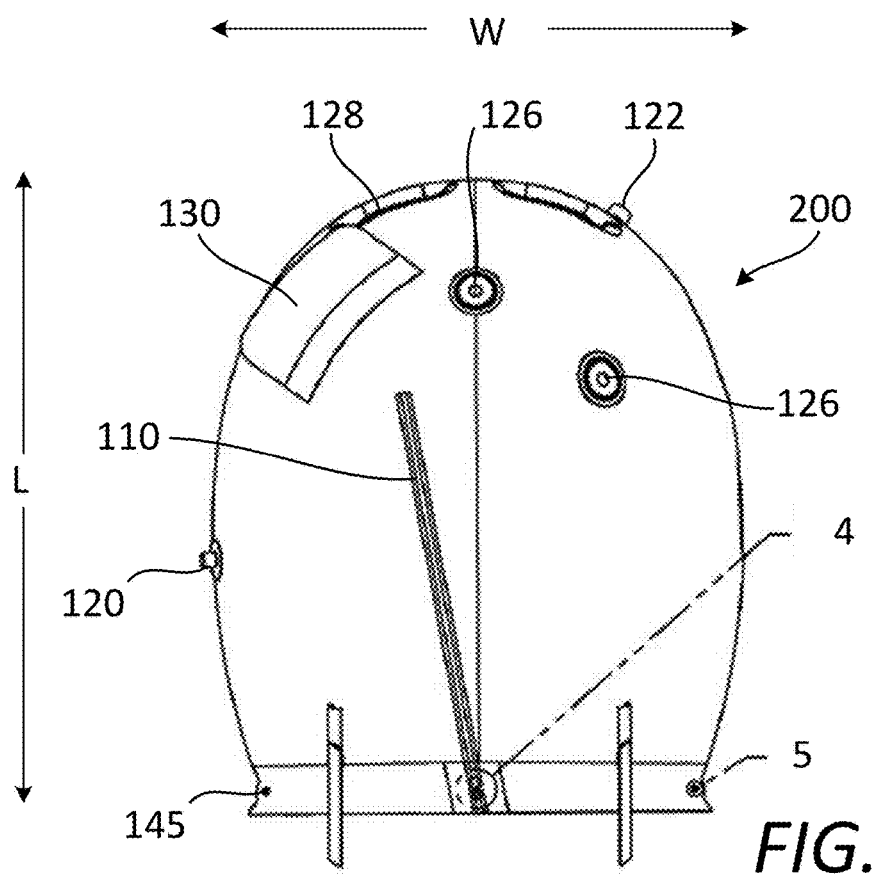
FIG. 3C is a top view of the PIPS apparatus of FIG. 3A.
Figure 3D:
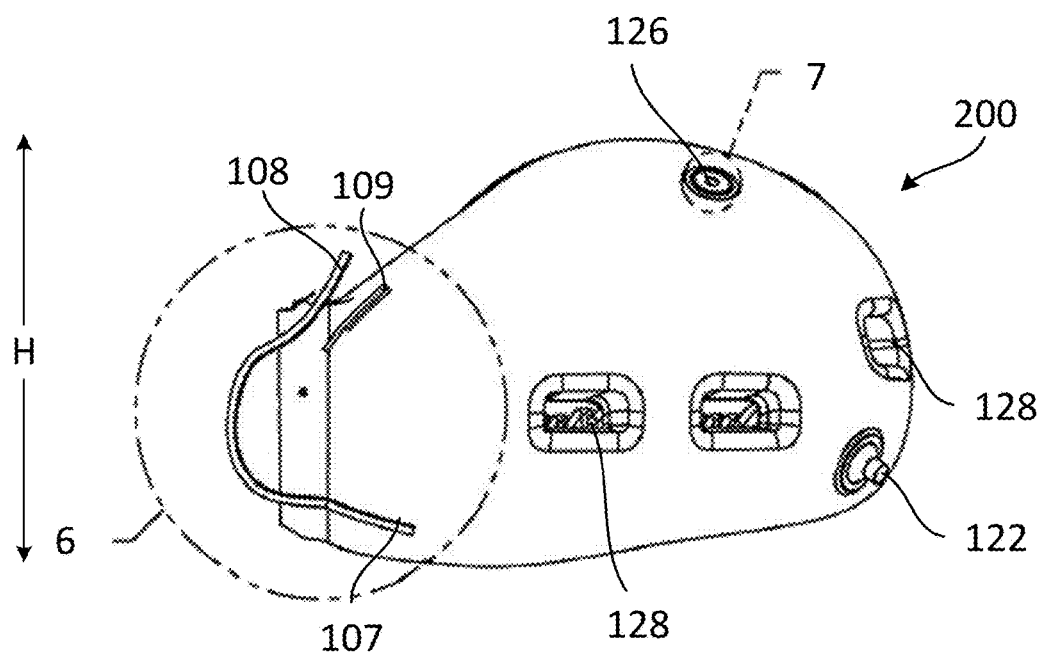
FIG. 3D is a side view of the PIPS apparatus of FIG. 3A.

FIG. 3C is a top view of the PIPS apparatus 200 showing dimensions width (W) and length (L). In one example W is between 60 and 90 cm. In another example W is between 70 and 80 cm. In one example L is between 80 cm and 120 cm. In another example, L is between 90 cm and 100 cm. FIG. 3D is a side view of the PIPS apparatus 200 showing height (H) dimension. In one example, H is between 50 cm and 80 cm. In another example, H is between 60 cm and 70 cm. In one example, W, L, and H, are dimensioned for pediatric patients.

FIG. 4 is an enlarged view of section 4 of FIG. 3C showing closure member 113, for example a zipper or zip-loc, or the like. In one example, closure member 113 is an airtight closure or zipper device, such as that made by Yoshida Company Ltd. (YKK, Japan). Unidirectional air flow valves at the air inlet and exhaust access ports prevent air outflow through either of these access port FIG. 5 is an enlarged view of section 5 of FIG. 3C showing inflation valve 140. In one example, inflation valve 140 is a luer connector configured to adapt to a syringe or pump for inflating cuff 112.

FIG. 6 is an enlarged view of section 6 of FIG. 3D showing the securing straps 106 with proximal end 107 coupled to sphere 200 outer surface. Strap 106 terminates at distal end 108. Distal end 108 is configured to secure to receiving member 109 positioned on opposite surface of sphere 200 than that of proximal end 107. This configuration allows for securing the sphere 200 about the patient 99. In one example, the strap 106 is positioned between the arms and torso of the patient to assist in securing and sealing open end 105 about the patient 99. In one example, distal end 108 is configured to pass thru inner and outer surfaces of cuff 112 for attachment to receiving member 109 as shown.

Figure 7:
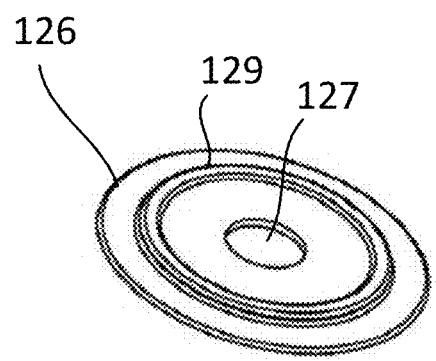
FIG. 7 is an enlarged view of a valve of FIG. 3D.

FIG. 7 is an enlarged view of one of the plurality of intubation ports 126 of FIG. 3D, for example, for administering oxygen, for providing a glide scope, providing suction and/or other respiration assistance and equipment. In one example, intubation port 126 is configured to provide an air-tight seal about the port and the device coupled thereto. Inlet port 120 is configured to couple with a powered air purifying respirator (PAPR) to provide filtered air to the patient. In one example, inlet port 120 is configured to couple to a self-contained breathing apparatus (SCBA) to provide filtered air to the patient. The PAPR device can be battery powered for portability with the sphere 100, 200 and can be provided together with the sphere or separately. In one example, the Powered Air Purifying Respirator (PAPR) is a 3M GVP-100 unit, equipped with a HEPA filter capable of filtering air of particles greater than 0.3, 0.2, 0.1 or 0.05 microns. In one example, the PAPR comprises an air purifier and blower device, a blower motor with a shaft for rotating fan blades to drive air into sphere 100, 200. In another example, the PAPR includes one or more air purifier devices or filters (FIG. 8B). In one example, inlet port 120 is an air valve with the air flow from the PAPR opening the valve to allow air flow into sphere 100, 200, thus, preventing reverse flow and providing immunocompromised patients with protection from ambient opportunistic infection.

In one example, the patient is provided with filtered air flow from a PAPR device at a predetermined rate. In one example, the flow rate of filtered air from the PAPR device is at a pressure so as to prevent excess carbon dioxide about the patient's head and to minimize or remove moisture and/or minimize or prevent fogging of the interior of the sphere. In one example, the flow rate of filtered air from the PAPR device is between 3-7 cubic feet/minute.

While air leakage of the sphere 100, 200 is inevitable, such leakage is kept within a predetermined range such that the sphere 100, 200 when positioned about the patient with a PAPR blower unit will provide for not more than 50%, 40%, 30%, 20%, or 10% of the air from escaping the sphere over a five-minute period after the stopping of the air flow into the sphere. The pressurized air flow from the PAPR inflates the sphere and prevents or minimizes contact of the sphere interior surface from contacting the patient.

Figure 8A:
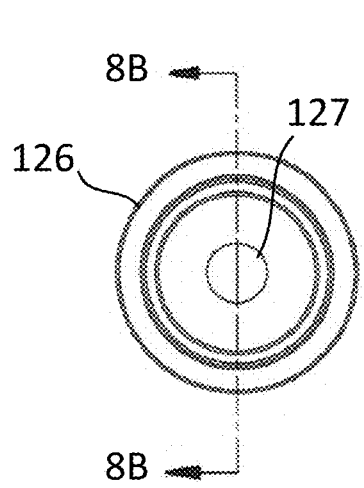
FIG. 8A is a top view of the valve of FIG. 7.
Figure 8B:
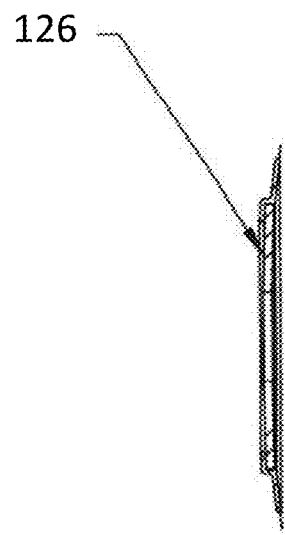
FIG. 8B is a cross-sectional view taken along the line 8B-8B of FIG. 8A.

FIG. 8A is a top view of the intubation port 126 of FIG. 7 showing self-sealing port 127 configured for sealing about the device. FIG. 8B is a cross-sectional view taken along the line 8B-8B of FIG. 8A. In one example, intubation port 126 has a threaded outer surface for receiving a threaded cap to hermetically seal the intubation port 126 until used.

Figure 9A:
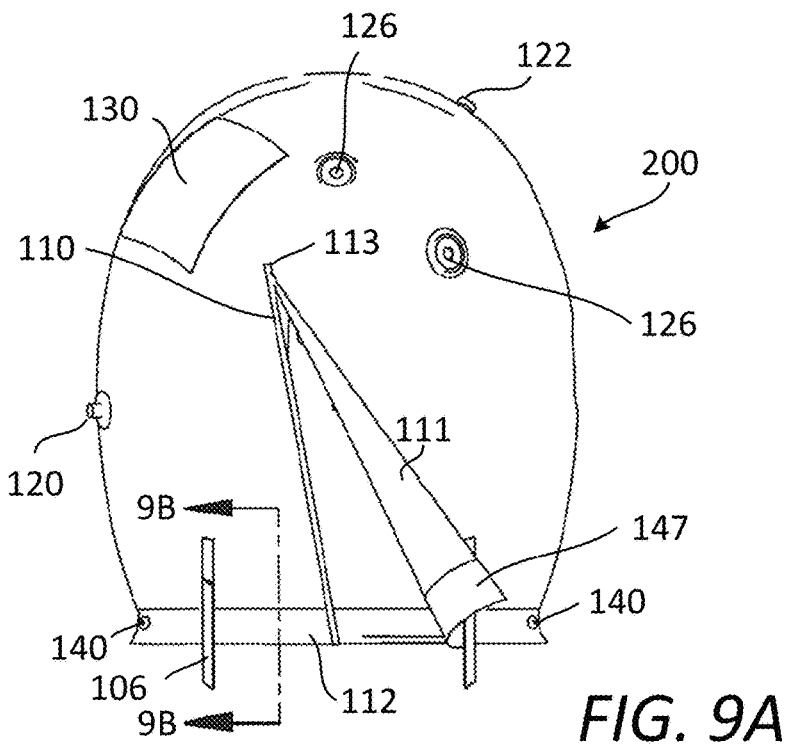
FIG. 9A is a top view the PIPS apparatus of FIG. 3C showing access of the apparatus.
Figure 9B:
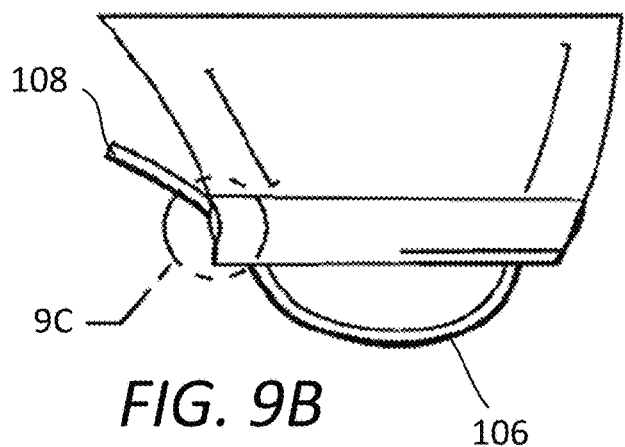
FIG. 9B is a cross-sectional view taken along the line 9B-9B of FIG. 9A.

FIG. 9A is a top view the PIPS apparatus 200 of FIG. 3C in an open configuration revealing inner surface 147 of cuff 112, where closure member 113 of accessing member 110 is shown in a fully open configuration. Section line 9B-9B. FIG. 9B is a cross-sectional view taken along section line 9B-9B thru cuff 112 of FIG. 9A which shows strap 106 passing thru cuff 112 for receiving by receiving member 109 (not shown).

Figure 9C:
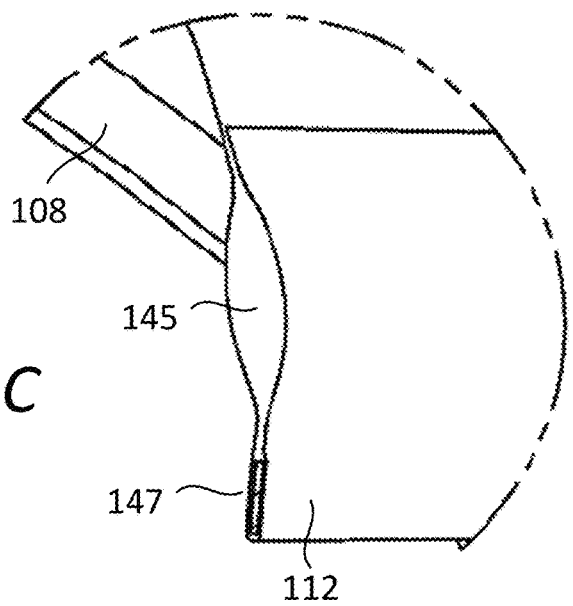
FIG. 9C is an enlarged view of section 9C of FIG. 9B.

FIG. 9C is an enlarged view of section 9C of FIG. 9B showing internal passageway of cuff 112 where flap 111 provides enlargement of open end 105 for receiving a patient. In one example, internal volume 145 of cuff 112 is inflated at port 140 to assist in sealing the cuff about the torso of the patient. In another example, the inner surface 147 of cuff 112 comprises a pressure sensitive adhesive material or is comprised of a cohesive surface that adheres to skin to assist or provide a seal of the cuff with the patient. In another example, cuff 112 comprises an elastomeric material to assist or provide a seal of the cuff with the patient.

Figure 10A:
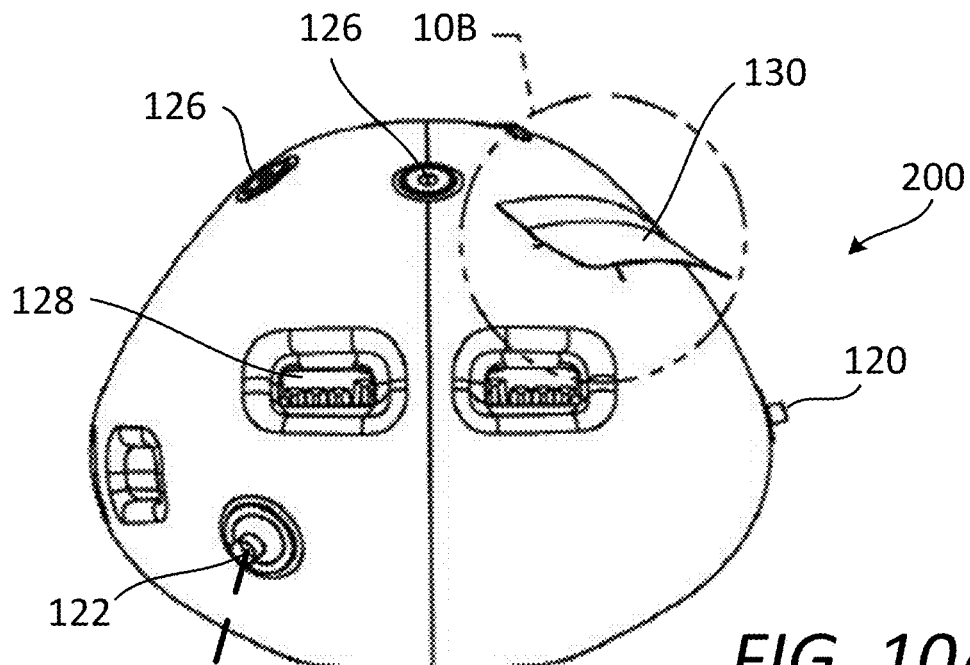
FIG. 10A is a closed end view of the PIPS apparatus of FIG. 3A.
Figure 10B:
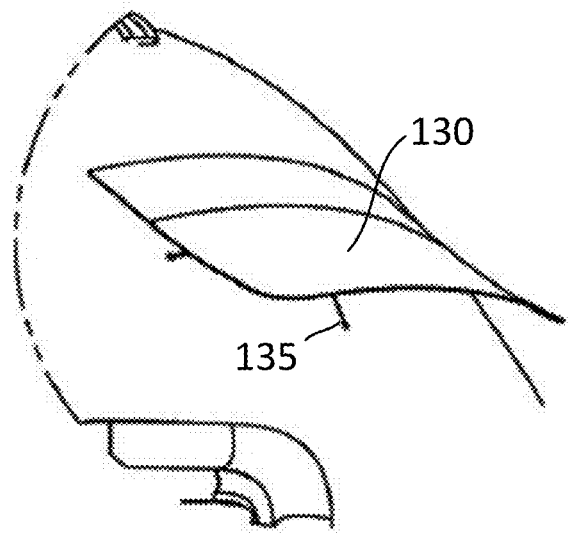
FIG. 10B is an enlarged view of section 10B of FIG. 10A.

FIG. 10A is the closed end view of the PIPS apparatus 200 showing hatch 130, intubation ports 126, air exit port 122 and air inlet port 120 as well as gloves 128. FIG. 10B is an enlarged view of section 10B of FIG. 10A emphasizing external access port or hatch 130 having self-sealing slit members 135 for allowing objects to be introduced and/or removed from the inside volume of sphere 100, 200. Other self-sealing configurations can be employed to allow objects to be introduced and/or removed from the inside volume of sphere 100, 200. Exit port 122 is shown optionally coupled to a filtered reservoir for trapping viral and/or pathogens that may contain activated charcoal/carbon or other chemical substances capable of neutralizing the viral and pathogenic organisms.

Figure 11:
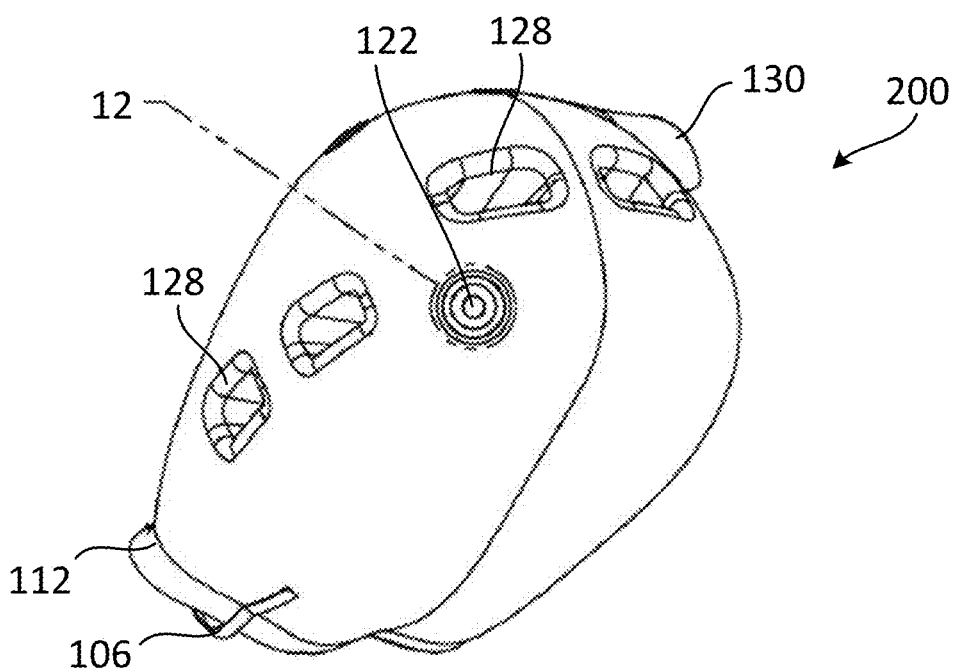
FIG. 11 is a perspective side view of the PIPS apparatus of FIG. 6.
Figures 12, 13:
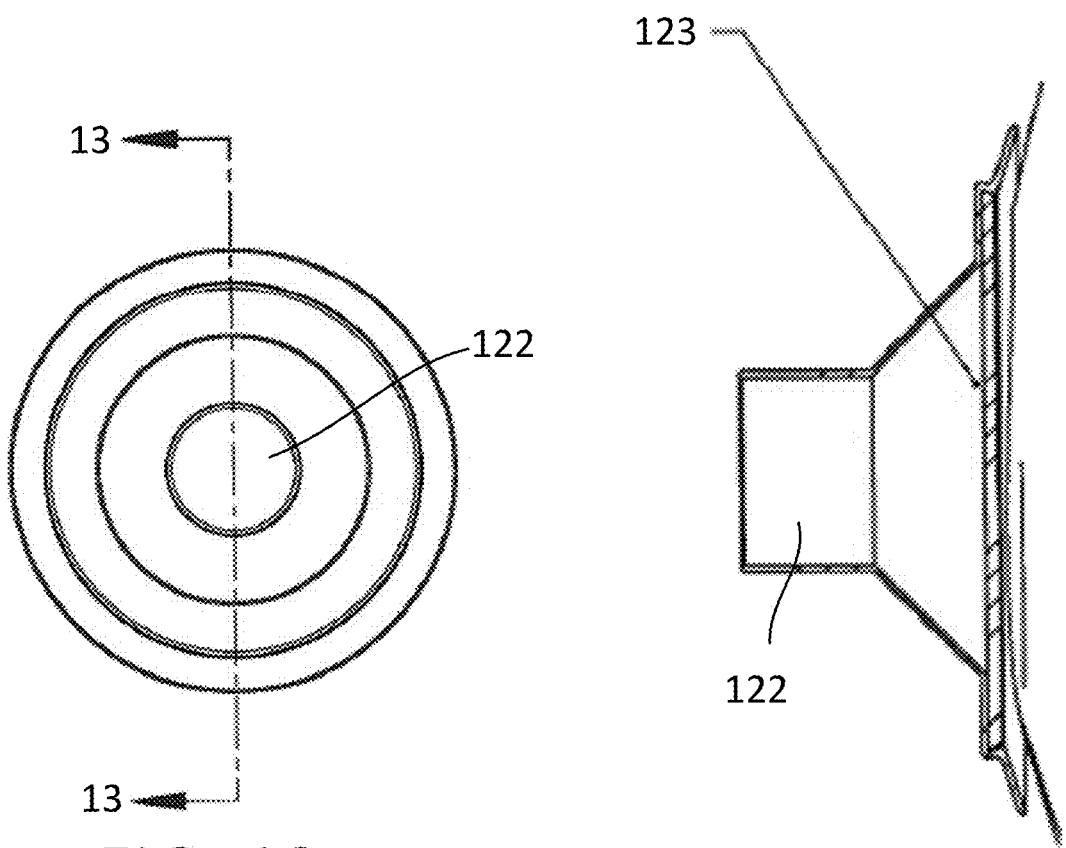
FIG. 12 is an enlarged view of a one way valve of FIG. 11.
FIG. 13 is a cross-sectional view taken along the line 13-13 of FIG. 12.

FIG. 11 is a perspective side view of the PIPS apparatus of FIG. 6 emphasizing exit port 122, shown in section 12. FIG. 12 is an enlarged view of section 12 showing a top view of exit port 122. In one example, as shown in FIG. 13, exit port 122-sectional view taken along the line 13-13 of FIG. 12 shows filter 123 configured to filter air exiting the sphere 100, 200 from exit port 123. In one example, filter 123 is configured as an exhaust outlet viral filter. In one example, filter 123 is configured as a large exhaust reservoir.

In one example, filter 123 is configured to filter particles of less than 0.5 μm average diameter, less than 0.1 μm average diameter or less than 0.01 μm average diameter. In one example, exit port 122 is a one way air valve configured to provide a desired air flow throughput and low back pressure within sphere 100, 200. In one example, exit port 122 is a one-way air valve which allows air flow in only one direction which is in the exit direction for the sphere 100, 200. Exit port 122 can be constructed of plastic, i.e., a hard rigid plastic housing portion or body with a central opening. In another example, exit port 122 is a check valve or other valve with similar function. In one example, filter 123 comprises activated charcoal/carbon or other chemical substances capable of trapping or neutralizing viral particles and other contagious materials.

In one example, transparent top surface 104, which is shown in FIG. 1A, is a flexible plastic. In one example, the flexible plastic is transparent or semi-transparent. In another example, the flexible plastic is substantially transparent or comprises portions of transparency. In another example, the flexible plastic is puncture resistant. In another example, the flexible plastic is polyvinyl chloride, polyacrylic, polymethacrylic, polycarbonate, polyethylene terephthalate (PET), polyethylene naphthalate (PEN), cyclic olefin copolymer (COC), polyethylene (PE; e.g., linear low density (LDPE), medium density PE, or high density PE), polyolefin copolymer, PET/LDPE, or nylon/LDPE. In another example, the flexible plastic is of a thickness to provide transparency and puncture resistance. In one example, the flexible plastic, at a thickness of 2-4 mil, has a tensile strength adequate to sustain moderate impact without ripping or puncturing. In one example, the flexible plastic is suitable for sterilization by electron beam, gamma, ethylene oxide, or hydrogen peroxide processes.

In one example, the sphere, when inflated is devoid of any bendable, semi-rigid, arcuate struts or ribs as support to maintain a generally open inflatable position about the patient. Air flows into the inlet port 120 from PAPR blower and passes over patient's head and face before exiting from exit port 122. In one example, inlet air and exit air is filtered to remove or reduce particulate matter entering and leaving the sphere 100, 200 to reduce or eliminate contamination of the patient from the ambient environment as well as protecting health care workers from contagion from the patient.

As is understood, the apparatus 100,200 provides is a barrier to the passage of contaminants into or from the interior of the isolation sphere 100, 200 in which the patient is located. As shown, apparatus 100,200 covers the upper torso and head and portions of the arms of a patient. The present apparatus 100, 200 can be deployed and provide functional intubation including inflation of tube cuff, similar in speed to that of performing real-time human intubation. The presently disclosed device mitigates airway manager's exposure to aerosolized biological agents as well as reducing or eliminating operating room and/or emergency facility contamination when airway resuscitation is required. In one example, the presently disclosed device prevents or reduces potential exposure to TB, viral infections such as COVID-19, SARS, MERS, and influenza. In another example, the presently disclosed device prevents or reduces exposure to off-gassing toxic fumes, or nerve agents i.e., organophosphates etc. present on or emanating from the patient. In one example, all equipment deployed during intubation is retained in the sphere 100,200 upon its removal from the patient for proper disposal.

Real time COVID-19 patient intubation is provided deploying the presently disclosed device with intubation execution without airway complications, achievement of first pass intubation, attaining verification of tube position by end-tidal CO2 (EtCO2) detection and/or colorimetry while retaining patient isolation.

The presently disclosed device provides a storable, sterile, pliable, light weight, transparent and rapidly deployable intubation device to deploy quickly as needed. In another example, the presently disclosed device is configured for disposable, one-time use, where the entirety of the device comprises sustainable and/or recyclable material.

The presently disclosed device can be manufactured using conventional plastic sheet forming techniques, for example, extrusion blow molding. The device can be constructed in sections that can be subsequently welded together to form airtight seals as is known in the art using ultrasonic, solvent, or chemical bonding techniques.

The presently disclosed device is deployed in a manner so as to provide a method of intubating a patient. Thus, at least a portion of a patient is introduced to the inside volume of the device as previously described. At least a portion of the cuff is secured to at least a portion of the patient's torso. The securing straps are positioned between the arms and torso of the patient and secured to the receiving members of the spherical compartment. Powered air is connected to the at least one inlet port and the inside volume of the spherical compartment is inflated. At least one medical device is coupled to the at least one access port such that the respiratory orifices of the patient are isolated from an ambient environment. The order of the steps previously described can be different and/or one or more steps can be eliminated or substituted with other steps of similar function.

Although the above disclosure has been presented in the context of exemplary embodiments, it is to be understood that modifications and variations may be utilized without departing from the spirit and scope of the invention, as those skilled in the art will readily understand. Such modifications and variations are considered to be within the purview and scope of the appended claims and their equivalents.

What is claimed is:

1. A disposable, isolating intubation device, the device comprising:

a flexible, spherical compartment inflatable from a collapsible, folded state, the flexible, spherical compartment being substantially transparent and having a closed end and an open end distal from the closed end defining an inside volume for receiving a head, shoulders and a portion of a torso of a patient;

a cuff proximal to the open end; the cuff providing for closing of the flexible, spherical compartment about the torso to provide a barrier about the patient therein;

at least one inlet port on the spherical compartment configured for receiving powered air;

at least one exit port on the spherical compartment configured for releasing air from the inside volume;

at least one access port on the spherical compartment configured for coupling with medical devices; and at least one pair of gloves coupled with the spherical compartment and projecting into the inside volume;

wherein the cuff comprises a inflation port configured to receive air and to inflate the cuff.

2. The intubation device of claim 1, further comprising a substantially airtight zipper extending lengthwise from a location at the cuff to at least partially between the open end and the closed end.

3. The intubation device of claim 1, further comprising at least one selectively openable hatch on the flexible spherical compartment for receiving and removing objects from the inside volume.

4. The intubation device of claim 1, wherein the spherical compartment is comprised of a transparent polymeric material.

5. The intubation device of claim 1, wherein the cuff comprises at least two securing straps spaced from each other, the at least two securing straps proximally coupled to the spherical compartment on a first side thereof and distally securable to the spherical compartment on a second side thereof.

6. The intubation device of claim 1, wherein the cuff comprises an adhesive or cohesive surface for adhering to the patient.

7. The intubation device of claim 1, wherein the at least one inlet port receives air from an air blowing device at an airflow rate to inflate the flexible spherical compartment and maintains separation from the flexible spherical compartment and the patient's body.

8. The intubation device of claim 1, wherein the at least one inlet port receives air from a powered air purifying respirator (PAPR) or self-contained breathing device.

9. The intubation device of claim 1, wherein the at least one inlet port is a one-way airflow device to prevent a reverse flow of air from the inside volume.

10. The intubation device of claim 1, wherein the at least one exit port is a one-way airflow device to prevent a reverse flow of air from the ambient environment.

11. The intubation device of claim 1, wherein the at least one exit port is coupled to a reservoir.

12. The intubation device of claim 1, wherein the at least one exit port is coupled to an expandable reservoir.

13. The intubation device of claim 1, wherein the at least one inlet port and/or the at least one exit port further comprise at least one filter for filtering air being presented to the inside volume or the air exiting therefrom, respectively.

14. The intubation device of claim 13, wherein the at least one filter is configured to reduce or eliminate introduction of an infectious disease from the ambient atmosphere or to the ambient atmosphere.

15. The intubation device of claim 1, wherein the at least one access port receives intubation equipment, optical equipment, an oxygen line, a suction line, or electrical leads.

16. The intubation device of claim 1, wherein the at least one pair of gloves is positioned in proximity to the patient's head.

17. A method of intubating a patient comprising the steps of:

(a) introducing a head, shoulders and a portion of a torso of a patient to the inside volume of a device comprising:

a flexible, spherical compartment inflatable from a collapsible, folded state, the flexible, spherical compartment being substantially transparent and having a closed end and an open end distal from the closed end defining an inside volume for receiving the head, shoulders and the portion of a torso of the patient;

a cuff proximal to the open end; the cuff providing for closing of the flexible, spherical compartment about the torso to provide a barrier;

at least one inlet port on the spherical compartment configured for receiving powered air;

at least one exit port on the spherical compartment configured for releasing air from the inside volume;

at least one access port on the spherical compartment configured for coupling with medical devices; and at least one pair of gloves coupled with the spherical compartment and projecting into the inside volume;

(b) securing the cuff to the torso;

(c) connecting powered air to the at least one inlet port;

(d) inflating the inside volume; and (e) coupling at least one medical device to the at least one access port;

wherein the patient's respiratory orifices are isolated from an ambient environment; and wherein the cuff comprises a inflation port configured to receive air and to inflate the cuff.

* * * * *